(12) United States Patent
Minteer et al.

(10) Patent No.: US 8,702,792 B2
(45) Date of Patent: Apr. 22, 2014

(54) DRUG DELIVERY FROM ELECTROACTIVE MOLECULARLY IMPRINTED POLYMER

(75) Inventors: Shelley D. Minteer, Pacific, MO (US); Jenny Ulyanova, Saint Louis, MO (US)

(73) Assignee: Saint Louis University, St. Louis, MO (US)

(*) Notice: Subject to any disclaimer, the term of this patent is extended or adjusted under 35 U.S.C. 154(b) by 0 days.

(21) Appl. No.: 13/427,620

(22) Filed: Mar. 22, 2012

(65) Prior Publication Data

US 2012/0197180 A1 Aug. 2, 2012

Related U.S. Application Data

(60) Continuation of application No. 12/266,349, filed on Nov. 6, 2008, now Pat. No. 8,216,300, which is a division of application No. 11/372,653, filed on Mar. 10, 2006, now Pat. No. 8,252,045.

(60) Provisional application No. 60/660,800, filed on Mar. 12, 2005.

(51) Int. Cl.
*A61F 2/06* (2013.01)

(52) U.S. Cl.
USPC ........................................... 623/1.42

(58) Field of Classification Search
USPC ................... 977/904, 906; 623/1.42
See application file for complete search history.

(56) References Cited

U.S. PATENT DOCUMENTS

| | | | |
|---|---|---|---|
| 4,487,667 | A | 12/1984 | Traynor |
| 4,519,938 | A | 5/1985 | Papir |
| 4,837,096 | A | 6/1989 | Kimura et al. |
| 6,063,637 | A | 5/2000 | Arnold et al. |
| 6,314,317 | B1 | 11/2001 | Willis |
| 6,582,971 | B1 | 6/2003 | Singh et al. |
| 6,605,236 | B1 | 8/2003 | Smith et al. |
| 2004/0020785 | A1 | 2/2004 | Minteer |
| 2004/0101741 | A1 | 5/2004 | Minteer et al. |
| 2005/0095466 | A1 | 5/2005 | Minteer et al. |

OTHER PUBLICATIONS

Edmund A. Debler and Abel Lajtha "High-Affinity Transport of y-Aminobutyric Acid, Glycine, Taurine, L-Aspartic Acid, and L-Glutamic Acid in Synaptosomal (P2) Tissue: A Kinetic and Substrate Specificity Analysis" Journal of Neurochemistry, vol. 48, No. 6, 1987, pp. 1851-1856.*

Tayhas, G., et al., "Microbial and Enzymatic Biofuel Cells," ACS Symp Ser 1994; 566:271-290.

Hepel, M., "Application for the Electrochemical Quartz Crystal Microbalance for Electrochemically Controlled Binding and Release of Chlorpromazine from Conductive Polymer Matrix," Microchemical Journal, 1997, pp. 54-64, vol. 56, Academic Press.

Witt, S., et al., "Conserved arginine-516 of Penicillium amagasakiense glucose oxidase is essential for the efficient binding of b-D-glucose," Biochem. J. (2000) 347, pp. 553-559.

Lee, H.S., et al., "Chiral and electrokinetic separation of amino acids using polypyrrole-coated adsorbents," Journal of Chromatography A, 2000, pp. 189-196, vol. 868, Elsevier.

Pernaut, J., et al., "Use of Conducting Electroactive Polymers for Drug Delivery and Sensing of Bioactive Molecules. A Redox Chemistry Approach," J. Phys. Chem, B 2000, pp. 4080-4090, vol. 104.

Zhang, S., et al., "In vivo monitoring of the monoamine neurotransmitters in rat brain using microdialysis sampling with liquid chromatography electrochemical detection," Analytica Chimica Acta, 2001, pp. 45-53, vol. 427, Elsevier Science B.V.

Vidal, J., et al., "Recent Advances in Electropolymerized Conducting Polymers in Amperometric Biosensors," Microchim. Acta, 2003, pp. 93-111, vol. 143, Springer-Verlag.

Lorenzo, Carmen Alvarez, et al., "Molecularly Imprinted Polymers for Drug Delivery," Journal of Chromatography, Dec. 2003, p. 231-245.

"TCM Gets a Modern Look," China Daily, May 18, 2005, (www.china.org.cn/english/scitech/129169.htm), printed on May 19, 2005, 3 pgs.

Moore, Christine M., et al., "Microchip-Based Ethanlo/Oxygen Biofuel Cell," RSC Publishing 2005 (www.rsc.org/publishing/journals/LC/article.asp?doi=b412719f), printed on May 20, 2005, 1 pg.

Heller, Dr. Adam, "Implantable Biofuel Cell Electrodes," (www.darpa.mil/dso/trans/energy/pa_uta.htm), printed on May 20, 2005, 3pgs.

International Search Report, International Patent Application No. PCT/US2006/08810, mailed on Jul. 3, 2008, 10 pages.

* cited by examiner

*Primary Examiner* — Thane Underdahl
(74) *Attorney, Agent, or Firm* — Lewis, Rice & Fingersh, L.C.

(57) ABSTRACT

A device delivers a chemical or biological agent, the device comprises an imprint molecule (IM) to be delivered by the device; an electroactive molecularly imprinted polymer (EMIP) imprinted with the imprint molecule, the EMIP having a plurality of binding sites capable of binding the imprint; and an electric potential producing member (EPM), the EPM being capable of producing an electric potential between the EPM and the EMIP; whereby when the EMIP has a predetermined density of imprint molecule bound at the binding sites, and whereby when a sufficient potential is produced between the EPM and the EMIP, the imprint molecule is released from the binding site and thereby delivered by the device.

9 Claims, 5 Drawing Sheets

DRUG DELIVERY FROM ELECTROACTIVE MOLECULARLY IMPRINTED POLYMER

CROSS REFERENCE TO RELATED APPLICATION(S)

This application is a Continuation of U.S. patent application Ser. No. 12/266,349, filed Nov. 6, 2008 and now U.S. Pat. No. 8,216,300, which is a Divisional of U.S. patent application Ser. No. 11/372,653 filed Mar. 10, 2006 and now U.S. Pat. No. 8,252,045, which is turn claims benefit of U.S. Provisional Patent Application Ser. No. 60/660,800, filed on Mar. 12, 2005 and now expired. The entire disclosure of all the above documents is incorporated herein by reference.

STATEMENT REGARDING FEDERAL SPONSORSHIP

Not Applicable.

BACKGROUND

1. Field of the Invention

The invention relates to electroactive molecularly imprinted polymers, and methods and devices using the same for the release of chemical or biological agents. More specifically, the invention embodies devices that utilize a molecularly imprinted polymer to release a chemical or biological agent in response to an electrical signal.

2. Description of Related Art

Most traditional medical therapies involve the administration or dosing of drugs at regular intervals, e.g., once daily or more frequently, and not generally in response to changing conditions within a patient. Time release formulations, which include polymer matrices, coated granules, and microcapsules have been developed to help maintain consistent effective plasma levels of a therapeutic agent over time. However, given that disease is generally defined as a disruption in the consistencies of homeostasis, neither traditional medical therapies nor time release formulations are optimally effective.

For the treatment of insulin-dependent diabetes, patients can use a somewhat more targeted treatment approach (also applicable in some other disease treatments) in which they measure their blood glucose levels at various times throughout the day, and administer an appropriate amount of insulin based upon the glucose concentration at that particular sampling time. Such a system is not optimal, however, for at least two reasons; firstly, it depends upon patient compliance, and secondly, it depends upon analyte (glucose) sampling that is periodic rather than continuous.

Modern drug delivery is moving toward the use of "smart" drug delivery devices. These devices monitor the amount of an analyte in the body and deliver an agent in response to a particular level of analyte. "Smart" drug delivery is important in the treatment of a number of diseases, diabetes and asthma being two prime examples. Both diseases are treated with drugs that have a narrow therapeutic range, because an inappropriately high concentration can have serious adverse effects. U.S. Pat. No. 6,314,317 teaches one such "smart" drug delivery device. That patent teaches an electroactive polymer having an electroactive pore, through which a therapeutic agent (e.g., a drug) may pass. The pore is controlled by a biologically active electron transfer agent (i.e., an analyte). The biologically active electron transfer agent is capable of transferring an electric charge to the electroactive polymer to enable the electroactive pore to open to allow the release of an agent. Thus, that invention is limited to analytes that interact with electroactive agents such as enzymes, and specifically oxidoreductases (e.g., glucose as an analyte and glucose oxidase as the biologically active electron transfer agent), and their respective therapeutic agents (e.g., insulin).

There is a long felt need for small, implantable "smart" drug delivery devices that release a therapeutic agent in response to changing levels of any one or more of a large number of analytes in a biological system. The need has generally still been unmet, and especially so with respect to analytes that do not have associated therewith a specific electroactive agent, such as many neurotransmitters.

SUMMARY

In an embodiment, the present invention is a device for delivery of a chemical or biological agent comprising a first imprint molecule (IM) comprising the chemical or biological agent to be delivered by the device; a first electroactive molecularly imprinted polymer (EMIP) imprinted with the first imprint molecule and having a plurality of binding sites, each of the binding sites being capable of binding the first imprint molecule in a manner characterized by a predetermined binding affinity between the binding site and the first imprint molecule; and an electric potential producing member (EPM), the EPM capable of producing an electric potential between the EPM and the EMIP; wherein the EMIP has a predetermined density of imprint molecules bound at the binding sites; and wherein when a sufficient potential is produced between the EPM and the EMIP, the binding affinity is decreased so that the first imprint molecule is released from the binding site and thereby delivered by the device. In an embodiment of such a device, either of the binding sites or the imprint molecules are capable of transitioning between at least a first electroconformation and a second electroconformation, such transition altering the binding affinity, and such transition being effected by application of the sufficient potential produced between the EPM and the EMIP.

In various embodiments, the first electroactive molecularly imprinted polymer is capable of participating in electron transfer, is capable of undergoing a redox reaction at the binding site, or is classified as a conducting polymer. In an embodiment, the electroactive molecularly imprinted polymer is of the class termed polyazine, and may be specifically one of poly (methylene green), poly (methylene blue), poly (neutral red) or poly (phenol red). In alternate embodiments the EPM is selected from the group consisting of a potentiometer, a biofuel cell, and an EMIP.

In further alternate embodiments, the delivery of the chemical or biological agent is dependent upon the detection of an analyte as a result of the potential produced by the EPM being dependent upon the detection of the analyte. In an embodiment wherein agent delivery is dependent upon detection of an analyte, the EPM is a second electroactive molecularly imprinted polymer imprinted with a second imprint molecule and having a plurality of binding sites, each binding site being capable of binding the second imprint molecule in a manner characterized by a certain binding affinity between the binding site and the second imprint molecule, and wherein the binding of the imprint molecule in the binding site allows for the generation of the potential. In an embodiment, either of the second imprint molecule or the binding site of the second electroactive molecularly imprinted polymer can transition between a first electroconformation and a second electroconformation, such transition altering the binding affinity between the binding site of the second electroactive molecularly imprinted polymer and the second imprint molecule. In an embodiment wherein agent delivery is dependent upon detection of an analyte, the EPM is a biofuel cell.

An alternate embodiment includes a method of delivering a chemical or biological agent comprising providing a device for delivery of a chemical or biological agent, said device comprising an electroactive agent-release element; a chemical or biological agent; and a means for producing electric potential electrically connected to the electroactive agent-release element; activating the means for producing electric potential so as to generate an electric potential between the means for producing electric potential and the electroactive agent-release element; transferring an electric charge between the means for producing electric potential and the electroactive agent-release element as a result of the step of activating; and releasing a chemical or biological agent from the electroactive agent-release element as a result of the step of transferring. In an alternate embodiment of the method, the electroactive agent-release element comprises an electroactive molecularly imprinted polymer having a plurality of binding sites, each binding site being capable of existing in either a first electroconformation or a second electroconformation, and the method further comprises the step of converting at least one of the binding sites from the first electroconformation to the second electroconformation as a result of the step of transferring. Yet another alternate embodiment of the method further comprises the steps of placing the device in an environment including an analyte of interest; and sensing the analyte of interest with the means for producing electric potential; wherein the means for producing electric potential is an analyte sensor that senses the analyte, and wherein the step of activating is a result of the step of sensing. In an alternate embodiment of the method, the step of sensing does not involve the analyte being either oxidized or reduced.

BRIEF DESCRIPTION OF THE FIGURES

FIG. 1 shows a schematic of a device for delivering an agent in response to an applied voltage.

FIG. 2 depicts a schematic of a device for delivering an agent in response to a change in the concentration of an analyte.

DETAILED DESCRIPTION OF EMBODIMENTS OF THE INVENTION

I. Electroactive Molecularly Imprinted Polymers

Figure 1A:
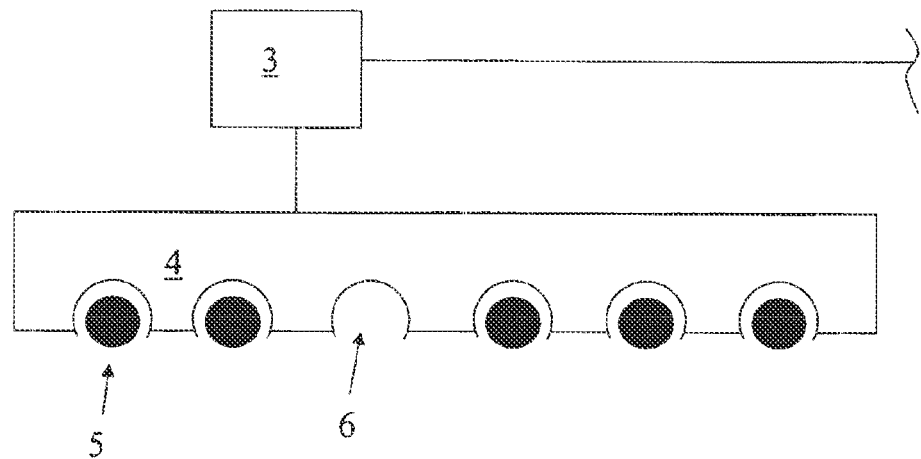
FIG. 1A shows the device prior to a sufficient potential being applied.

Among the various aspects of the present invention is an electroactive molecularly imprinted polymer (EMIP). The class of EMIP is comprised by the broader class of molecularly imprinted polymers (MIP), which are well known in the chemical arts. The production of MIP is generally described in Ye and Haupt, "Molecularly Imprinted Polymers and Receptor Mimics for Assays, Sensors and Drug Discovery," Anal. Bioanal. Chem. 378:1887-1897, 2004; Shi et al, "Template-imprinted Nanostructured Surfaces for Protein Recognition," Nature 398:593-597, 1999; Kandimalla and Ju, "Molecular Imprinting: A Dynamic Technique for Diverse Applications in Analytical Chemistry," Anal. Bioanal. Chem. 380:587-605, 2004; and Kriz et al., "Molecular Imprinting: New Possibilities for Sensor Technology," Analytical Chemistry, 69:345A-349A, 1997; all of which are incorporated herein by reference to the extent not inconsistent herewith.

Generally an MIP is formed by performing a polymerization in the presence of an imprint molecule (IM). The IM is incorporated into the polymer in a three-dimensional space constructed about the IM during polymerization. The IM generally is not covalently bound to the polymer during polymerization, but is incorporated within the polymer matrix and held by various electrical and mechanical forces within a three-dimensional space termed a binding site.

Under certain environmental conditions, the IM will either remain bound within the binding site, or may disassociate therefrom, potentially diffusing out of the polymer matrix. Thus, an MIP generally can exist with various amounts of IM incorporated therewithin, from none to an amount at which all of the binding sites are occupied, and further (to the extent that the polymer can incorporate IM within the matrix but outside of identified binding sites) to a point of saturation, at which point no more IM can be incorporated in the polymer matrix, and including various amounts therebetween.

A. Binding Sites in MIP

Binding of the IM in the binding site is generally a product of intermolecular interactions including hydrogen bonding and the attractive action of Van der Waals forces. Other interactions including other electronic forces (e.g., ionic interactions) and steric interactions may also have a role in binding. While not a limit on the present invention, a theory is that binding of the IM in the binding site is caused primarily as a result of hydrogen bonding. During polymerization, the molecules that form the MIP become arranged in a low energy state that is impacted by the specific intermolecular interactions between the MIP and the IM, including hydrogen bonding. A particular location within the MIP at which these interactions occur is a binding site. Upon disruption of these intermolecular interactions, a bound IM is able to disassociate from the binding site. In an opposite action, an unbound IM can become bound through a re-creation of these binding interactions.

B. Imprint Molecules

Another aspect of the invention is an imprint molecule (IM). The IM is a molecule present during polymerization of an MIP that is not polymerized nor covalently bound to the polymer matrix, but rather is a molecule about which the MIP forms. During polymerization, the IM provides certain molecular scale physical and electrical constraints on the polymer matrix, thereby helping to create a binding site. For MIP in which IM binding is the result primarily of hydrogen bonding, the IM preferably is capable of significant hydrogen bonding with the portion of the MIP within the binding site. In such cases the IM preferably includes more than one hydrogen atom covalently bound to an electronegative atom, the hydrogen atom thereby being able to form a hydrogen bond with an electron density (such as an electron density about an electronegative heteroatom) at the binding site. In an alternate environment, the IM provides an electron density that can bind with hydrogen atoms on the polymer matrix and within the binding site.

There is no particular limit on the molecule used as an IM. For larger IM molecules, however, a smaller proportion of the whole of the IM interacts with the polymer at a binding site, such that, for large molecules, even degradation products of the IM will be bound at the binding site, if such degradation products are present. Thus MIP produced using large molecule IM will be less selective for the IM than will MIP produced using small molecule IM.

C. Electroactive Polymers

As a subset of molecularly imprinted polymers (MIP), electroactive molecularly imprinted polymers (EMIP) is a class limited to those MIP that are electroactive. An EMIP is an MIP capable in some fashion of participating in an electric charge transfer. An EMIP certainly includes those MIP which are termed conducting, i.e., those MIP capable of conducting electricity, no matter the level of conductivity. Additionally, EMIP include those MIP for which at least some portion of the polymer is capable of undergoing electrochemical reduction or oxidation.

U.S. Pat. No. 4,519,938, which is incorporated herein by reference, describes polymers that may be used in the practice of an embodiment of this invention. Such polymers include, but are not limited to polyaniline, polypyrrole, polythiophenes, polyethylenedioxythiophene, and poly(p-phenylene vinylene). More preferably, polymers to be used in embodiments include poly(methylene green) ("PMG"), poly(methylene blue) ("PMB"), poly(phenol red) ("PPR"), and poly(neutral red) ("PNR"). Generally preferred polymers are those based on monomers having a high degree of conjugation, specifically including highly conjugated polycyclic monomers. These polymers allow for imprint formation, i.e., the formation of a binding site in the polymer matrix about the IM, that provides a three-dimensional shape conforming to and enhancing the binding interactions between the IM and the polymer matrix, creating an MIP that is more selective for the IM than for MIP based on monomers having a simpler structure. A class of preferred polymers can be generally termed polyazines. For embodiments that are to be used in connection with drug delivery in a living organism, it is preferred that the electroactive polymer be biocompatible. PMG is an example of a biocompatible EMIP.

D. EMIP Binding Site

While binding sites in MIP have been described generally above, in an embodiment of an EMIP of the invention, a binding site will have at least two stable or semi-stable states of being, such states of being defined by characteristics including physical conformation, electronic energy state, and chemical structure. In such an embodiment, the binding site is able to convert from one such state to another, wherein the difference between the states involves a difference in one or more of the physical conformation, electronic energy state, or chemical structure of the binding site. Such a change in the state of the binding site preferably affects the binding affinity for the IM.

In a preferred embodiment, at least two of the states of being of the binding site have significantly different binding affinities for the IM over a wide range of environmental conditions. As an example, in a first state the binding site affinity for the IM is relatively high, such that disassociation of the IM from the binding site is a rare event, while in a second state the binding site affinity for the IM is relatively low, such that disassociation of the IM from the binding site is likely. In such an embodiment, where the state of the binding site can be controlled, so too, the disassociation of the IM can be controlled.

In a more preferred embodiment, a transition of the binding site between a first state and a second state can be effected by application of an electric potential to the EMIP, application of the potential resulting in the binding site undergoing a redox reaction. For example, by applying an electric potential to an EMIP, a binding site may undergo an electrochemical reduction reaction, therein accepting transfer of an electron, as well as undergoing a transition from a first state to a second state. In this example, if the second state of the binding site, obtained as a result of the reduction reaction, has a sufficiently low binding affinity for the IM, the IM is likely to be released from the EMIP.

The various states of being of a binding site are referred to as electroconformations. As used herein, the term electroconformation is used to mean any and all characteristics of a molecular entity, or a portion thereof, such as the binding site of an EMIP, that correlate with the binding affinity as between an IM and an EMIP binding site. These characteristics may include but are not limited to physical conformation, electronic energy state, and chemical structure, which enumerated characteristics are not intended to limit the meaning of electroconformation as understood by one of ordinary skill in the art. In an embodiment, a change in electroconformation at the binding site is induced in response to a charge transfer. The charge transfer may be between the EMIP and a chemically independent (i.e., non-chemically bound) molecule or material, such as a redox catalyst or an IM, or may be within the EMIP. For example, the binding site of an EMIP may undergo a change in physical conformation in response to a charge transfer from direct connection to a DC voltage source. In another example, a hydroxyl moiety at the binding site may be oxidized to a carbonyl as a result of a charge transfer. Where such a hydroxyl moiety is located in the binding site of the EMIP and is involved in hydrogen bonding with the IM, such an oxidation will affect the binding affinity between the IM and the binding site, since the hydroxyl hydrogen atom will no longer be available for to participate in hydrogen bonding.

II. Drug Delivery Device

A. Comprising an Electroactive Agent-Release Element (EARE).

An EMIP such as described above may be particularly useful in a drug delivery device in which delivery of the drug is mediated by electron charge transfer. In an embodiment, such a charge-transfer mediated drug delivery device includes an electroactive agent-release element ("EARE") from which the drug is released. In an embodiment, an EMIP as described above is the EARE ("EMIP-EARE"), providing a medium from which controlled release of an IM is possible. In an embodiment useful as a drug delivery device, the IM is a drug, such as a therapeutic pharmaceutical agent. Since the binding and release of an IM from the EMIP is the result of one or more interactions between the IM and the EMIP, controlled release of the IM from the EMIP-EARE may be possible through control of various factors effecting the binding interaction between the EMIP-EARE and the agent. For example, controlled release of a pharmaceutical agent that is an IM may be exercised through control of the electroconformation of the binding site of the EMIP-EARE or of the pharmaceutical agent. Generally, control of the electroconformation of the IM, whether a pharmaceutical agent or other agent, would allow control of the release of the IM.

While the example device just described above is one for drug delivery, the devices and methods herein disclosed are aimed generally at the delivery of a chemical or biological agent. The agent is not limited to being a therapeutic pharmaceutical agent. The disclosed methods and devices are applicable to any and all situations wherein one would want to control the release of a chemical or biological agent. The invention encompasses many applications where a chemical or biological signal is designed to be produced (release of the agent) in a controlled fashion, including pharmaceutical drug delivery and further including, but not limited to, environmental air, water, or soil systems, and industrial processes. Because the molecular imprinting of a polymer is readily accomplished with IM having a wide range of chemical structures, the applications of a device that allows a controlled release of IM are numerous.

Figure 1B:
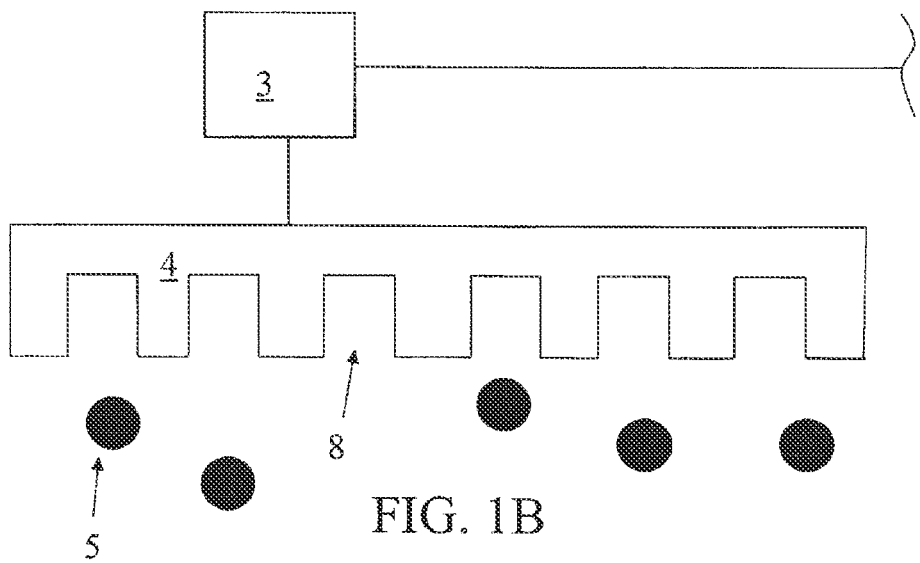
FIG. 1B shows release of the agent as a result of a sufficient potential being applied.

In an embodiment, control of the binding site is provided via the generation of an electrical potential between an EMIP-EARE and another element within its environment. Thus, with reference to an embodiment shown in FIG. 1, a drug delivery device comprises an EMIP-EARE 4, an IM 5, and an electric potential producing member ("EPM") 3. Initially, as shown in FIG. 1A, the binding site of the EMIP-EARE 4 is in a first electroconformation 6 (represented by a semi-circular shape), in which the binding site has a higher affinity for the IM 5. Under specified conditions, which may be user controlled, the EPM 3 produces an electric potential that is sufficient to generate charge transfer to or from the EMIP-EARE 4. In an embodiment, as a result of this charge transfer, the binding site of the EMIP-EARE 4 undergoes a change in electroconformation from the first electroconformation 6 to the second electroconformation 8 (represented as three sides of a square), as shown in FIG. 1B. In the second electroconformation 8 of this example embodiment, the binding site has a sufficiently decreased binding affinity for the IM 5 that the IM 5 may diffuse away from the EMIP-EARE 4. A working example of such a device is described in Example 1 below.

B. Comprising an Electroactive Sensing Element (ESE)

In another aspect of a drug delivery device, the release of an agent is dependent upon the presence of a certain analyte in the environment about the device. An embodiment of such a device comprises an analyte sensor that generates a signal as a result of the presence of a certain amount of an analyte in the environment about the sensor. The signal thus generated can then be used in the drug delivery device in effecting release of the drug. That is, the analyte sensor can act as the EPM 3, generating a change in electric potential as its signal. An analyte sensor for such use is more generally referred to as an electroactive sensing element ("ESE"). In an embodiment of a drug delivery device an ESE is the EPM 3 ("ESE-EPM"), which upon detection of the analyte changes the electric potential between the ESE-EPM and the EARE.

Figure 2A:
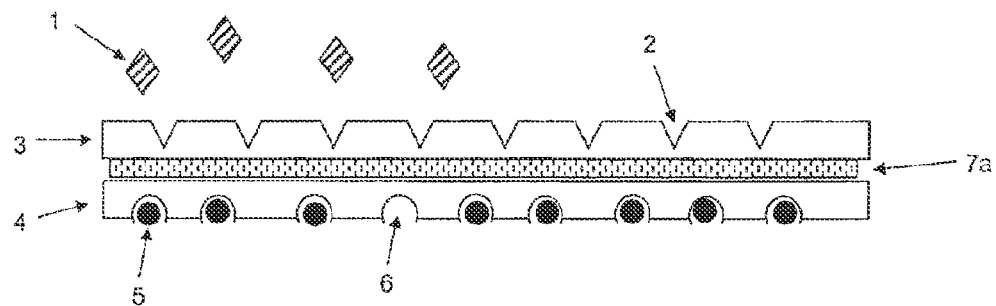
FIG. 2A shows the device when the analyte is not at a concentration required to generate a release of the agent.
Figure 2B:
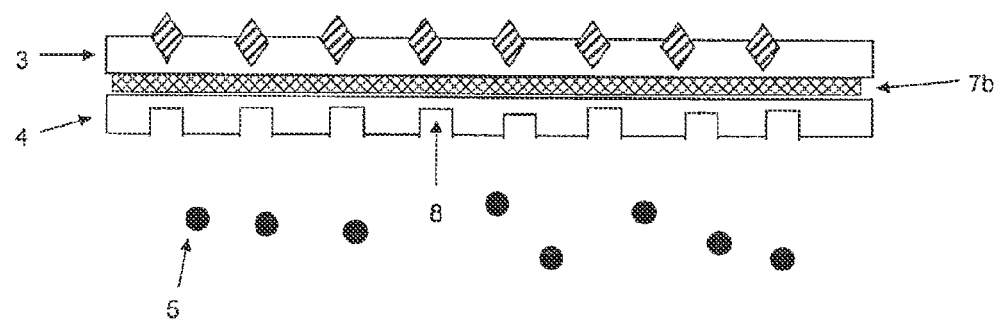
FIG. 2B shows the device when the analyte is at a concentration allowing a release of the agent.

In an embodiment of a charge-transfer mediated drug delivery device a charge transferred to the EARE is produced by an ESE. Thus, in an embodiment as shown in FIG. 2, a drug delivery device comprises an EARE 4 that is an EMIP, an IM 5, and an EPM 3 that is an ESE. In this embodiment, as described above, the IM 5 is first bound to the EMIP-EARE 4, but is released when the EMIP-EARE 4 undergoes a change in electroconformation. In this embodiment the change in electroconformation is the result of an electron transfer from the ESE 3. That is, the ESE 3 produces electrons that can be transferred to the EMIP-EARE 4. Electrons are transferred after the potential between the ESE 3 and EMIP-EARE 4 reaches a given threshold value, which occurs when the analyte 1 is at a particular concentration, or is at a concentration that is at or above a particular threshold concentration, or is within a particular concentration range of concentrations (each of which circumstance is hereinafter referred to as having the analyte at a "particular concentration"). In an embodiment, when the analyte concentration is not at the particular concentration required to generate the threshold potential, electrons are generally not transferred, and the binding sites of the EMIP-EARE 4 generally do not change electroconformations.

In an embodiment, such a device is connected to a patient's circulatory system, for example, as an implantable device positioned within the flow of blood in a vein or artery, or as a device mounted external to the patient's body but having direct access to a vein or artery. In an embodiment, the device detects the level of an analyte in the blood of the patient and delivers a drug to the patient in response thereto. In such an embodiment, the analyte may be any analyte believed to be related to a physiological symptom or condition that is to be treated with the drug released by the device. By way of a non-limiting example, the analyte may be a substance such as a neurotransmitter, hormone, autocrine factor, paracrine factor, fatty acid, such as cholesterol and linoleic acid, adrenocortical hormone, or other molecule-of-interest (e.g., catecholamines, epinephrine, norepinephrine, serotonin, dopamine, NO, pyruvate, glucose, short or long chain alcohol, and the like).

1. Biofuel Cell Sensor

In an embodiment, the ESE is a biofuel cell comprising an anode and a cathode, wherein the anode is a bioanode comprising an oxidoreductase enzyme sequestered within an enzyme immobilizing material. Preferably, the biofuel cell comprises both a bioanode and a biocathode, wherein the biocathode also comprises an oxidoreductase enzyme sequestered within a enzyme immobilizing material. Biofuel cells useful in the practice of this invention are described in copending U.S. patent application Nos. 60/429,829, 60/486,076, 60/517,626, 60/544,260, Ser. Nos. 10/617,452, and 10/931,147, U.S. patent application publication number 2004/0101741, and PCT patent applications PCT/US03/37336, and PCT/US04/037151, all of which are incorporated herein by reference. In such an embodiment, the biofuel cell is in electrical contact with the EARE such that the biofuel cell can deliver electrons to the EARE, effecting release of the agent. In an embodiment where the EARE is an EMIP, release of the agent occurs as described above (through electroconformational change) upon charge transfer from the biofuel cell to the EMIP-EARE.

In an embodiment, the biofuel cell delivers charge in an amount dependent upon the concentration of an analyte in the environment about the drug delivery device. An aspect of such a device is that the analyte regulates the release of the agent by directly or indirectly affecting the activity of the oxidoreductase enzyme of the biofuel cell electrode. The affect in activity may be the result of the analyte acting as an allosteric regulator, co-enzyme, substrate, or product. By way of non-limiting example, in a case wherein the oxidoreductase enzyme is a glucose oxidase, the analyte may be glucose, and the agent may be insulin. Oxidoreductase enzymes, substrates, allosteric regulators, co-enzymes and products useful in the practice of this invention are well known in the art. For a review, see *Practical Enzymology*, Hans Bisswanger, Wiley-VCH, Weinheim, Del., May 2004, which is incorporated herein by reference. In this way the biofuel cell-ESE may be used to regulate release of an agent wherein the analyte is not electroactive or has no particular electroactive complimentary agent. By way of a non-limiting example, the analyte may be a substance such as a neurotransmitter, hormone, autocrine factor, paracrine factor, fatty acid, such as cholesterol and linoleic acid, adrenocoritcal hormone, or other molecule-of-interest (e.g., catecholamines, epinephrine, norepinephrine, serotonin, dopamine, NO, pyruvate, glucose, short or long chain alcohol, and the like). Generally, see the above referenced U.S. and PCT applications and publications.

Another aspect of a drug delivery device as herein described is that it may be tuned to optimize delivery of the agent released therefrom. It is possible to alter the chemical composition of either of the EARE or the EPM to affect the electron transfer between these elements of the device, such as the potential necessary to effect an electron transfer to the EARE, the potential at which the EPM will deliver electrons, or the potential at which the binding sites undergo a change in electroconformation. Further the physical characteristics of either of these elements, such as the dimensions of the element in a particular device, and of the physical characteristics of any materials connecting these elements will further impact the rate or conditions under which the agent will be released.

2. EMIP Sensor

In another embodiment the ESE is an EMIP, the IM for which is the analyte of interest. Detection of the analyte 1 occurs when an unoccupied binding site becomes occupied by an IM, i.e., when binding occurs. In order for binding sites to bind IM, generally after the imprinting polymerization, the IM is disassociated from the EMIP-ESE. In an embodiment, disassociation is effected, for instance, by altering the chemical environment of the ESE. For example, the IM may be extracted from the EMIP-ESE by washing the EMIP-ESE with a solvent that disrupts the binding interactions between the IM and the binding site, so as to cause the IM to disassociate from the EMIP-ESE. Such a solvent may be characterized by pH, such that a raised or lowered pH value for the solvent may effect the disassociation.

After disassociation of the IM, the EMIP binding sites are available to bind again the IM. Then, if the EMIP-ESE is exposed to an environment containing the IM (as analyte), the EMIP-ESE may bind the IM. In a embodiment, the binding of the IM in the EMIP-ESE results in release of one or more electrons that can be transferred to the EARM resulting in release of a chemical or biological agent. In an embodiment the release of electrons occurs as a result of oxidation of the IM as it interacts with the binding site. In an alternate embodiment, the EMIP-ESE is oxidized as a result of binding the IM. In either case, oxidation releases electrons that then may be transferred through the ESE to the EARE. In an embodiment in which the EARE is an EMIP-EARE, the binding sites then undergo a change in electroconformation, which enables the release of the agent.

Figure 5:
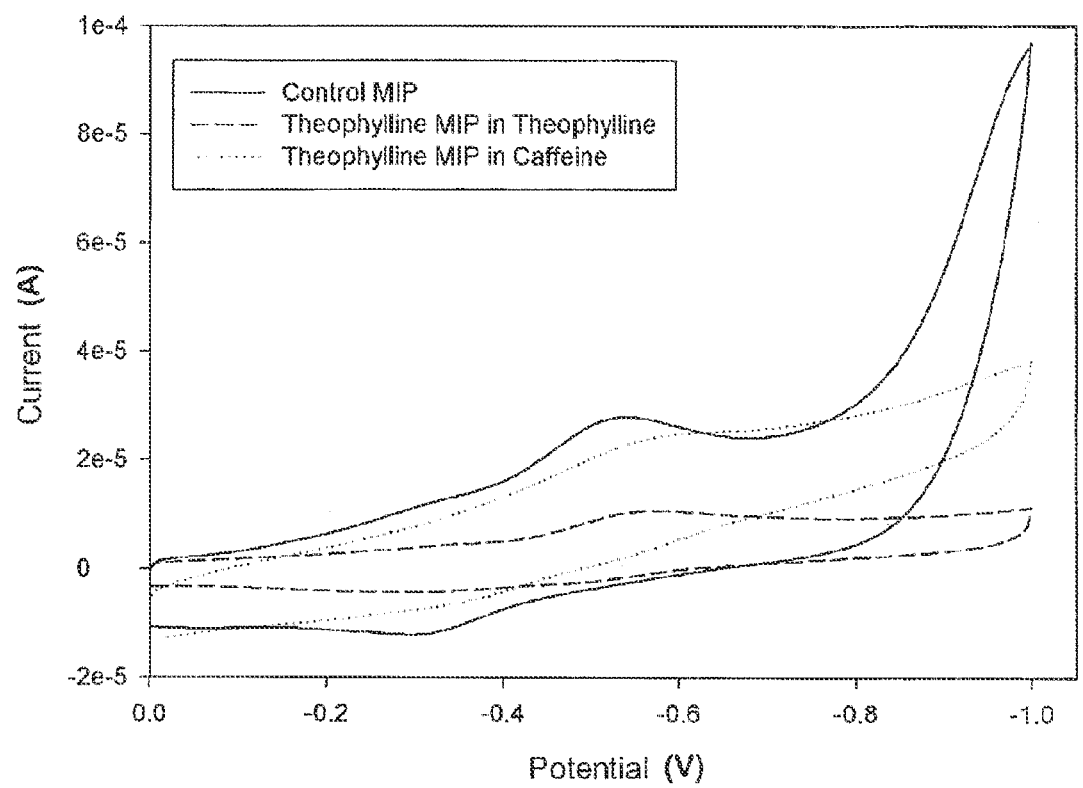
FIG. 5 shows cyclic voltammograms demonstrating the selectivity for theophylline of a theophylline imprinted polymer, such as might be used to detect theophylline as an analyte.

In order for an EMIP-ESE to be most effective in a drug delivery device, it should be selective for the analyte of interest. Indeed, EMIP are selective for their IM. As shown in the voltammograms in FIG. 5, an electrode coated with theophylline imprinted PMG binds theophylline from solution rather than allowing the theophylline to undergo electrochemical reaction. Thus, the electrode coated with theophylline imprinted PMG, when placed in a solution of theophylline, did not show significant current generation, as compared to an electrode coated with theophylline imprinted PMG placed in a solution containing caffeine. That is, the caffeine was not bound by the theophylline imprinted PMG to the same extent as was the theophylline, such that the caffeine could participate in electrochemistry, thereby allowing a current to develop.

III. Method Description

In another embodiment, the invention is directed to a method of delivering an agent 5 into a certain environment. In an embodiment, the method comprises producing an electric potential using an EPM, which potential is sufficient to generate an electron transfer to an EARE, allowing a binding site within the EARE to undergo an electroconformational change, reducing the binding affinity of the binding site for a bound IM by changing the electroconformation of the binding site, and releasing the IM from the binding site. In an alternate embodiment, the method comprises producing an electric potential with an EPM by contacting the EPM with an analyte, which potential is sufficient to generate an electron transfer to an EARE, allowing a binding site within the EARE to undergo an electroconformational change, reducing the binding affinity of the binding site for a bound IM, and thereby releasing the IM from the binding site. In this alternate embodiment, the analyte is preferably produced by a biological system, more preferably a patient, and most preferably a human patient. Where the environment is a patient, it is preferred that the method operate automatically within the patient as a result of a device comprising an EPM and EARE being implanted into the patient.

Example 1

Release of Theophylline from an Imprinted Poly (Methylene Green) Electrode

For this example, all potentials were measured against a saturated calomel electrode. The EARE for this example was created by coating theophylline imprinted PMG on one of four glassy carbon micro-electrodes formed on a microchip. The imprinted PMG coating was created by electro-polymerizing methylene green on the surface of the microelectrode by performing cyclic voltammetry from −0.3V to 1.3 V at a scan rate of 50 mV/s for 50 scan segments while the microelectrode was submerged in a solution that contained 0.04 mM methylene green and saturated theophylline in a 10 mM borate buffer. Electrochemical polymerization is a widely employed for the synthesis of polymers generally (see, e.g., U.S. Pat. Nos. 6,605,236, 6,383,415, and 4,487,667, and references therein, all of which are incorporated herein by reference). This method gives good control over the thickness of the polymer films, allows for direct deposition of the films on the electrode surface, and leads to greater stability of the polymer.

After forming the EARE by coating the electrode, the EARE was rinsed with 18 MΩ water and stored in pH 7.1-7.4 phosphate buffer, until being used for the study. No leaching of theophylline from the coated electrode was measured before the following experiment.

Figure 3:
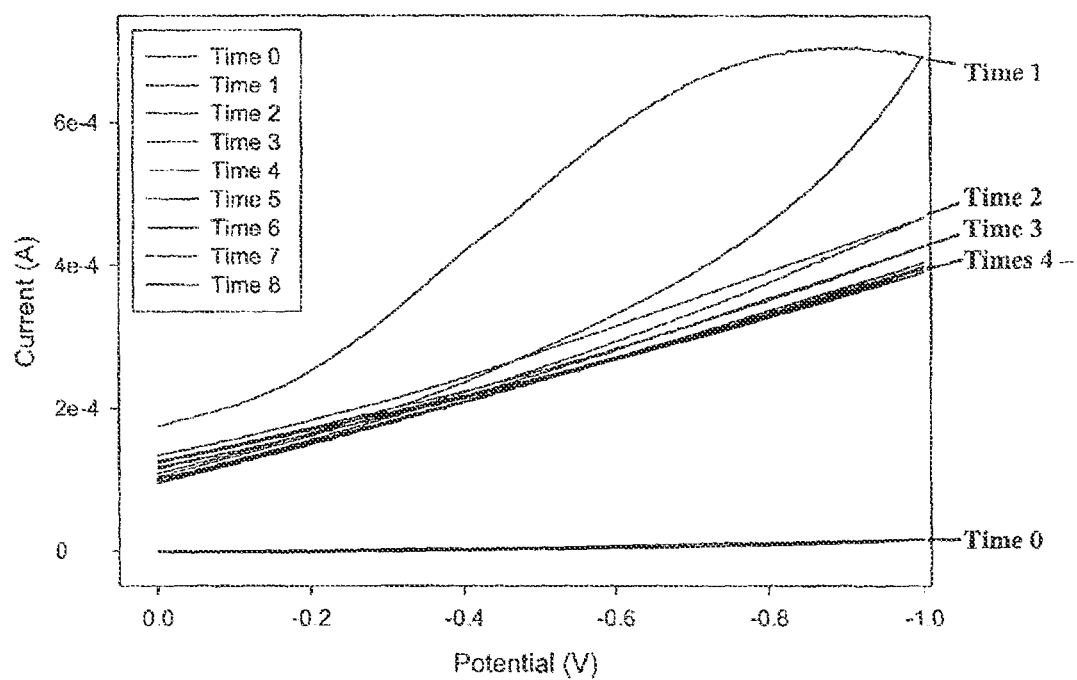
FIG. 3 depicts cyclic voltammograms indicating the release of theophylline from a poly (methylene green) ("PMG") coated electrode that is molecularly imprinted for theophylline as the result of a potential applied by a DC power supply.

To deliver the drug, a potentiometer applied a constant potential of −1.2 V to the coated electrode. Drug delivery was measured by taking a cyclic voltammogram every sixty seconds at an uncoated glassy carbon electrode that was positioned at a distance 20 microns from the theophylline-imprinted PMG coated electrode. Nine cyclic voltammograms were taken, one each minute for a period of nine minutes. FIG. 3 shows the results of the cyclic voltammetric scans. The first voltammogram at sixty seconds after applying the −1.2 V potential showed that a burst of released theophylline was detected at the bare electrode. The concentration of theophylline detected at the uncoated electrode decreased throughout the nine minute test period, as the imprinted theophylline was exhausted from the coated electrode.

Example 2

Biofuel Powered Drug Delivery Device

Figure 4:
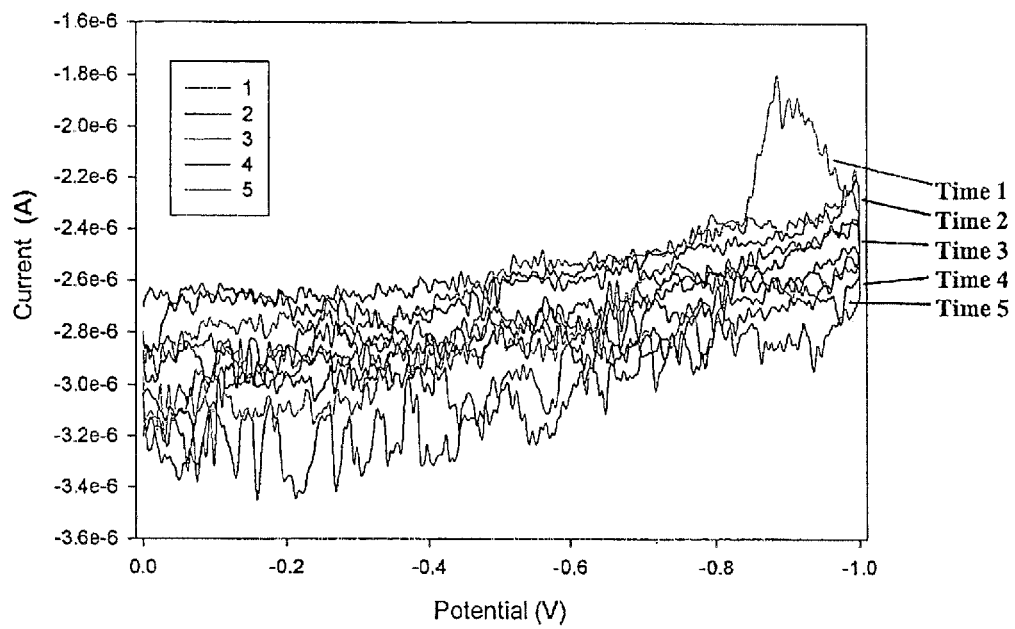
FIG. 4 shows cyclic voltammograms indicating the release of theophylline from a poly(methylene green) coated electrode based upon a potential applied from a bio fuel cell upon introduction of a 1 mM glucose solution thereto.

After set up of a drug delivery system as described in Example 1, such system was coupled to a glucose biobattery system (see U.S. and PCT patent applications referenced above) designed to deliver 1.5V at 1 mM glucose. A pH 7.15 buffer solution containing 1 mM glucose was added to the bio fuel cell, which generated a potential. As shown in FIG. 4, cyclic voltammograms collected at a sensing electrode 15 microns away from the drug delivery electrode show the delivery of theophylline as recorded at 60-second intervals over a 5-minute time period. Similar to the result of Example 1 (FIG. 3), FIG. 4 shows a spike of theophylline is delivered initially, and delivery of the drug decreases with time as the theophylline is expelled from the molecularly imprinted drug delivery electrode (EMIP-EARE).

While the invention has been disclosed in connection with certain preferred embodiments, the specific characteristics of these preferred embodiments should not be understood as limitations on all embodiments of the invention. Modifications and variations of the described embodiments may be made without departing from the spirit and scope of the invention, and other embodiments should be understood to be encompassed in the present disclosure as would be understood by those of ordinary skill in the art.

The invention claimed is:

1. A device for delivery of a chemical or biological agent comprising:
   a first imprint molecule comprising said chemical or biological agent to be delivered by said device into an environment in which said device is located;
   a second imprint molecule comprising an analyte present in said environment in which said device is located;
   a first electroactive molecularly imprinted polymer imprinted with said first imprint molecule, said first electroactive molecularly imprinted polymer also having a plurality of first binding sites capable of binding said first imprint molecule, each of said first binding sites characterized by a binding affinity between said first binding site and said first imprint molecule; and
   a second electroactive molecularly imprinted polymer imprinted with said second imprint molecule and having a plurality of second binding sites capable of binding said second imprint molecule, each of said second binding sites characterized by a certain binding affinity between said second binding site and said second imprint molecule;
   wherein binding of said second imprint molecule to said second electroactive molecularly imprinted polymer creates an electric potential between said second electroactive molecularly imprinted polymer and said first electroactive molecularly imprinted polymer;
   wherein said first electroactive molecularly imprinted polymer has a predetermined density of said first imprint molecules bound at said first binding sites;
   wherein when a sufficient potential is produced between said second electroactive molecularly imprinted polymer and said first electroactive molecularly imprinted polymer, electrons transfer from said second electroactive molecularly imprinted polymer to said first electroactive molecularly imprinted polymer causing said binding affinity between said first binding site and said first imprint molecule to decrease so that said first imprint molecule is released from said first binding site and thereby delivered by said device into said environment, and
   wherein said first electroactive molecularly imprinted polymer and said second electroactive molecularly imprinted polymer are conducting polymers.

2. The device of claim 1:
   wherein said first binding sites are capable of transitioning between at least a first electroconformation and a second electroconformation;
   wherein said binding affinity between said first imprint molecule and said first binding site existing in said first electroconformation is greater than said binding affinity between said first imprint molecule and said first binding site existing in said second electroconformation; and
   wherein said sufficient potential produced between said second electroactive molecularly imprinted polymer and said first electroactive molecularly imprinted polymer results in said transition of said first binding site between said first electroconformation and said second electroconformation.

3. The device of claim 1:
   wherein said first imprint molecule is capable of transitioning between at least a first electroconformation and a second electroconformation;
   wherein said binding affinity between said first binding site and said first imprint molecule existing in said first electroconformation is greater than said binding affinity between said first binding site and said first imprint molecule existing in said second electroconformation; and
   wherein said sufficient potential produced between said second electroactive molecularly imprinted polymer and said first electroactive molecularly imprinted polymer results in said transition of said first imprint molecule between said first electroconformation and said second electroconformation.

4. The device of claim 1, wherein said first electroactive molecularly imprinted polymer is capable of undergoing a redox reaction at said binding site.

5. The device of claim 1 wherein said environment is blood within a vein or artery.

6. The device of claim 1 wherein said analyte is related to a physiological symptom or condition.

7. The device of claim 6 wherein said first imprint molecule is a drug to treat said physiological symptom or condition.

8. The device of claim 1 wherein said analyte is selected from the group consisting of: a neurotransmitter, a hormone, an autocrine factor, a paracrine factor, a fatty acid, and an adrenocoritcal hormone.

9. The device of claim 1 wherein said analyte is selected from the group consisting of: catecholamines, epinephrine, norepinephrine, serotonin, dopamine, NO, pyruvate, glucose, short chain alcohol, and long chain alcohol.

* * * * *